United States Patent [19]

Warming

[11] 4,209,021
[45] Jun. 24, 1980

[54] APPARATUS FOR GENERATING AND MEASUREMENT OF DEFINED FORCES FOR MEDICAL APPLIANCES

[75] Inventor: Nils Warming, Hamburg, Fed. Rep. of Germany

[73] Assignee: J. D. Möller Optische Werke GmbH, Wedel, Fed. Rep. of Germany

[21] Appl. No.: 863,405

[22] Filed: Dec. 22, 1977

[51] Int. Cl.² .............................................. A61B 9/00
[52] U.S. Cl. ........................................ 128/652; 73/81
[58] Field of Search ............... 128/645, 646, 650, 651, 128/652, 774; 73/81

[56] References Cited

U.S. PATENT DOCUMENTS 3,308,653  3/1967  Roth ..................................... 128/643

OTHER PUBLICATIONS

"IRE Transactions on Medical Electronics", Apr. 1960, pp. 61–67.

Primary Examiner—George J. Marlo
Attorney, Agent, or Firm—Toren, McGeady and Stanger

[57] ABSTRACT

An apparatus for the generation and measurement of defined forces independent of position or travel of transmitting members for medical examination appliances wherein a lever pivotable about a horizontal axis in a vertical plane carries a probe adapted to be placed in contact with the body of a patient under controlled and measurable pressure. The lever is actuated by an electro-magnetic arrangement, limited in its movement electro-mechanically, and its torque is controlled and measured electronically. The apparatus includes a two-armed lever pivotally mounted about a horizontal axis for movement in a vertical plane, the center of gravity of the lever coincides with the pivot axis of the lever. A contact probe for engaging a body area under examination is attached to the free end portion of the upper arm of the lever. A permanent magnet system and a rectangular coil are secured to the free end of the lower arm of the lever. Electronic control and measuring circuitry energizes the coil and includes a voltage-controlled constant current source connected with a control indicator, an input keyboard for setting the output voltage of the electronic circuitry, maximum and minimum limiters and indicating means. The movement of the lever is mechanically controlled by a motor-driven cam plate serving as a detent. The lever movement about its pivot axis in the homogeneous field of the permanent magnet system is restricted. Within the operational range of the cam plate, a slide is secured to the free end of the lower arm of the lever and a light barrier.

3 Claims, 6 Drawing Figures

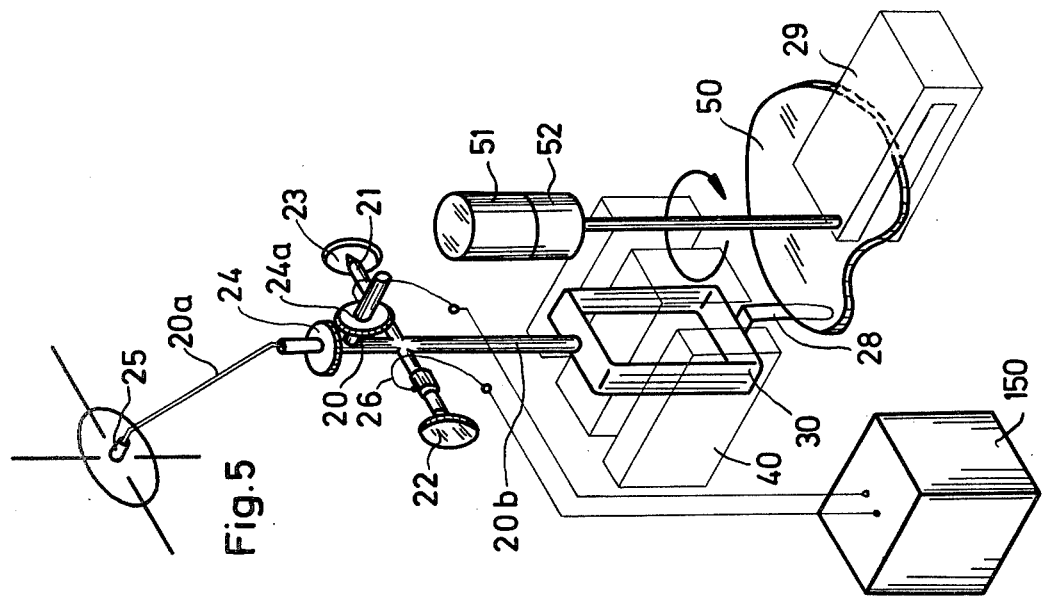
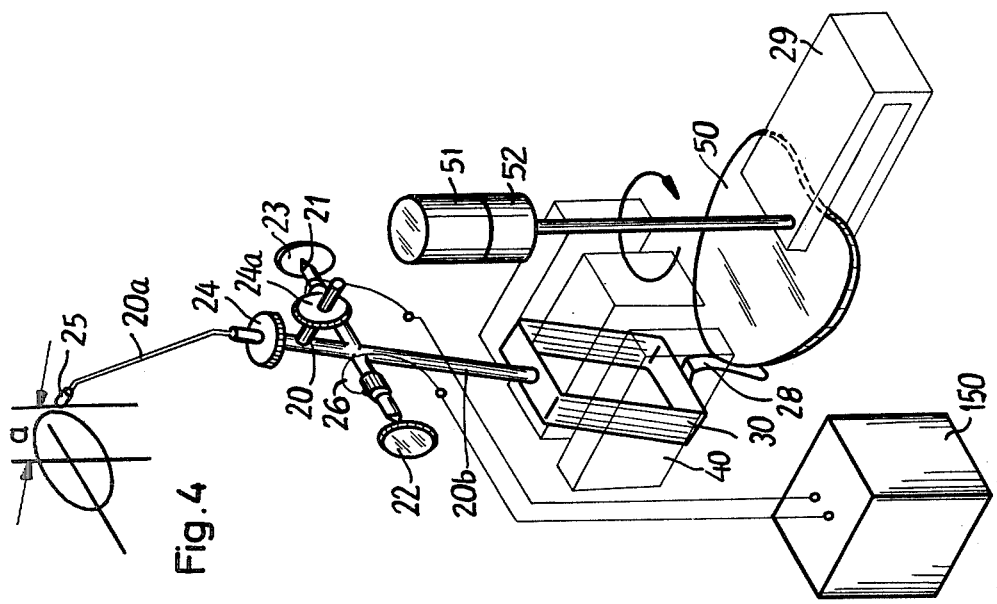

APPARATUS FOR GENERATING AND MEASUREMENT OF DEFINED FORCES FOR MEDICAL APPLIANCES

FIELD OF THE INVENTION

The present invention relates to an apparatus for the generation and measurement of defined forces independent of position or travel of transmitting members for medical examination appliances.

BACKGROUND OF THE INVENTION

It is known for pressure to be exerted on areas of a human body under examination with probes, such as feelers, stimulators, glass bulbs, of medical appliances, especially tonometers and esthesiometers. This can, for instance, be achieved by weights, weighted levers or other members under spring tension or subject to a collapsing force. The disadvantages of generating pressure in such manner lie in the inherent jolting pressure changes, in its compulsory direction and also in most cases in the patients having to lie down during the examination. With appliances equipped with springs, the distance between them and the patient is often a measure for the applied force; if these appliances are hand-held, an error frequently enters into the measured result caused by unsteady holding. It is also known to evaluate diverse buckling forces which result out of the insertion length of plastic threads. However, this leads to great inaccuracy, since the plastic threads are bent within themselves so that no real buckling forces need to be generated and also by the hygroscopic properties of the thread material.

All known appliances have the common disadvantage that simple and often desired subsequent electrical processing of the measured results is not directly possible.

It is therefore the object of the present invention to create an apparatus for the generation of a defined force and the measurement thereof in medical examination appliances independent of position or travel of transmitting members which avoids the disadvantages described above of the known appliances and which permits electric subsequent processing of the measured results.

In order to achieve this object, an apparatus is proposed for the generation and measurement of defined forces independent of position or travel of transmitting members for medical examination appliances which, according to the invention, embodies a combination of the following features:

(a) In a housing, a two-armed lever pivotably mounted about a horizontal axis for movement in a vertical plane, the center of gravity of the lever coinciding with the pivot axis of the lever, a contact probe for engaging a body area under examination attached to the free end portion of the upper arm of the lever;

(b) a force producing means including a permanent magnet system and a rectangular coil secured to the free end of the lower arm of the lever, the rectangular coil when moving the lever adapted to move, with at least one side portion, through a homogeneous magnetic field generated by the permanent magnet system, narrow strips of gold with a negligibly small resisting torque connecting the rectangular coil with electronic control and measuring circuitry;

(c) the electronic control and measuring circuitry for energizing the coil including a voltage-controlled constant current source connected with a control indicator, an input keyboard for setting the output voltage of the electronic circuitry, maximum and minimum limiters in the form of limit switches operatively coupled to the integrator, and indicating means such as a voltmeter;

(d) the extent of movement of the lever about its pivot axis in the homogeneous field of the permanent magnet system being adapted to being restricted;

(e) the movement of the lever being mechanically controlled by a motor-driven cam plate serving as detent, being connected with a motor control to effect controlled movements of the contact probe;

(f) the heart-shaped cam plate being connected to the motor through an interposed gear train;

(g) within the operational range of the cam plate, a slide being secured to the free end of the lower arm of the lever and a light barrier system for movement control of the lever being disposed.

It is possible with such apparatus in appliances for medical examination to generate and measure defined forces independent of position or travel of transmitting members and, subsequently, to process the measured results electrically. It is not necessary anymore that the patient lies down. Precise measurements are possible in all attitudes of the patient. Measuring errors which are normally caused by unsteady holding of examination equipment are avoided with the appliance according to the invention. A slide at the lower arm of the lever and light barriers controlling the lever movement being disposed within the operational range of the cam plate together achieve the advantage that the body area under examination absorbs the pressure while the cam plate continues to rotate until its widest part masks both light barriers. Then, the lever has its greatest freedom of movement and, when the key is released, the cam plate automatically reverses its rotation and lifts the contact probe off the body area.

BRIEF DESCRIPTION OF THE DRAWINGS

An embodiment of the present invention is illustrated in the drawings.

FIGS. 4, 5 and 6 show isometric views to further clarify the operation of the inventive apparatus.

DESCRIPTION OF THE PREFERRED EMBODIMENTS

Figure 1:
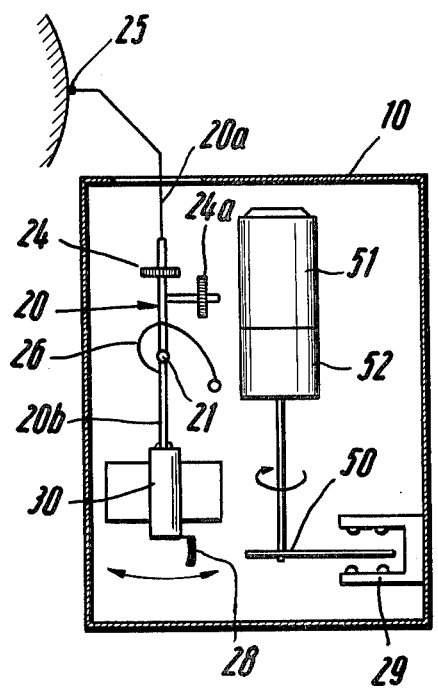
FIG. 1 is a schematic lateral elevation of an apparatus for the generation and measurement of defined forces independent of position or travel of transmitting members in medical examination appliances in accordance with the present invention.
Figure 2:
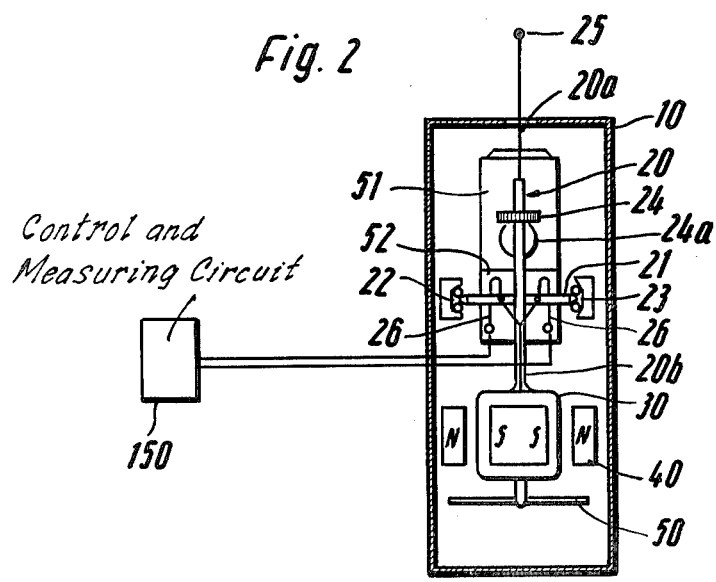
FIG. 2 is a schematic front elevation of the apparatus shown in FIG. 1.

Referring to FIGS. 1 and 2, the apparatus for the generation and measurement of a defined force independent of position or travel of transmitting members in medical examination appliances includes a housing 10 for the force generating and measuring system. This force generating and measuring system includes a two-arm lever 20 which is pivotable about a horizontal axis 21 and the upper arm 20a of which carries at its free end a contact probe 25, while its lower arm 20b carries a rectangular coil 30 of a force generating device which consists of this rectangular coil and a permanent magnet system 40. The axis 21 is held in bearings 22, 23 within the interior of the housing 10. The center of gravity of the lever 20 coincides with its axis 21; its behavior is therefore quite independent of its position. Adjustment screws 24, 24a are provided for a one-time adjustment of the center of gravity (refer to FIG. 1). The bearings 22, 23 for the pivot axis 21 of the lever 20 are of the low friction type.

The swivelling range of the lever 20 is limited in such way that the travel of the contact probe 25 at the end of the upper lever arm 20a, which is longer than the lower lever arm 20b, amounts to approximately ±10 mm.

The generation of force is effected in a generating device which, as already mentioned above, consists of the coil 30 and the permanent magnet system 40. The two long sides of coil 30, or at least one of them, are movably disposed in the air-gap and therefore within the homogeneous field of the magnet system 40. The energizing power for the coil 30 is fed through narrow gold strips 26 which exert only a negligibly small resisting torque on the lever 20. Force is only transmitted to the probe 25 when a current flows through coil 30. Force F is a function of the coil current $I_C$, I the length of the magnetic field, B the magnetic flux, and N the number of windings of coil 30. Therefore:

$$F = I_C \times N \times I \times B$$

Thus Force F is proportional to the coil current $I_C$. A variation of the coil current causes a change of force. This results in a linear relationship within the measuring range used. The torque, and therefore the force because of the constant length of the lever, is independent of the pivoting angle within the desired tolerances.

The rotation of lever 20 around its pivoting axis 21 is limited to the homogeneous part of the field of the permanent magnet system. This is achieved by a motor-actuated stop which controls the freedom of movement of lever 20 and thereby the movement of the contact probe 25. This limiter of the lever movement consists of a cam plate 50 serving as detent which is positioned by a motor 51. A gear train 52 is interposed between the cam plate 50 and the motor 51. The movement profile of the motor, such as rotational speed etc., is subject to control (refer to FIGS. 1 and 2).

The force as determined by the set current is exerted initially against the cam plate 50 serving as detent. It is turned in such manner by the motor 51 and the interposed gear train that the probe 25 moves towards the area of examination with a defined speed. When the probe 25 touches the body area aimed at this takes the load off the detent and absorbs the set pressure.

Figure 3:
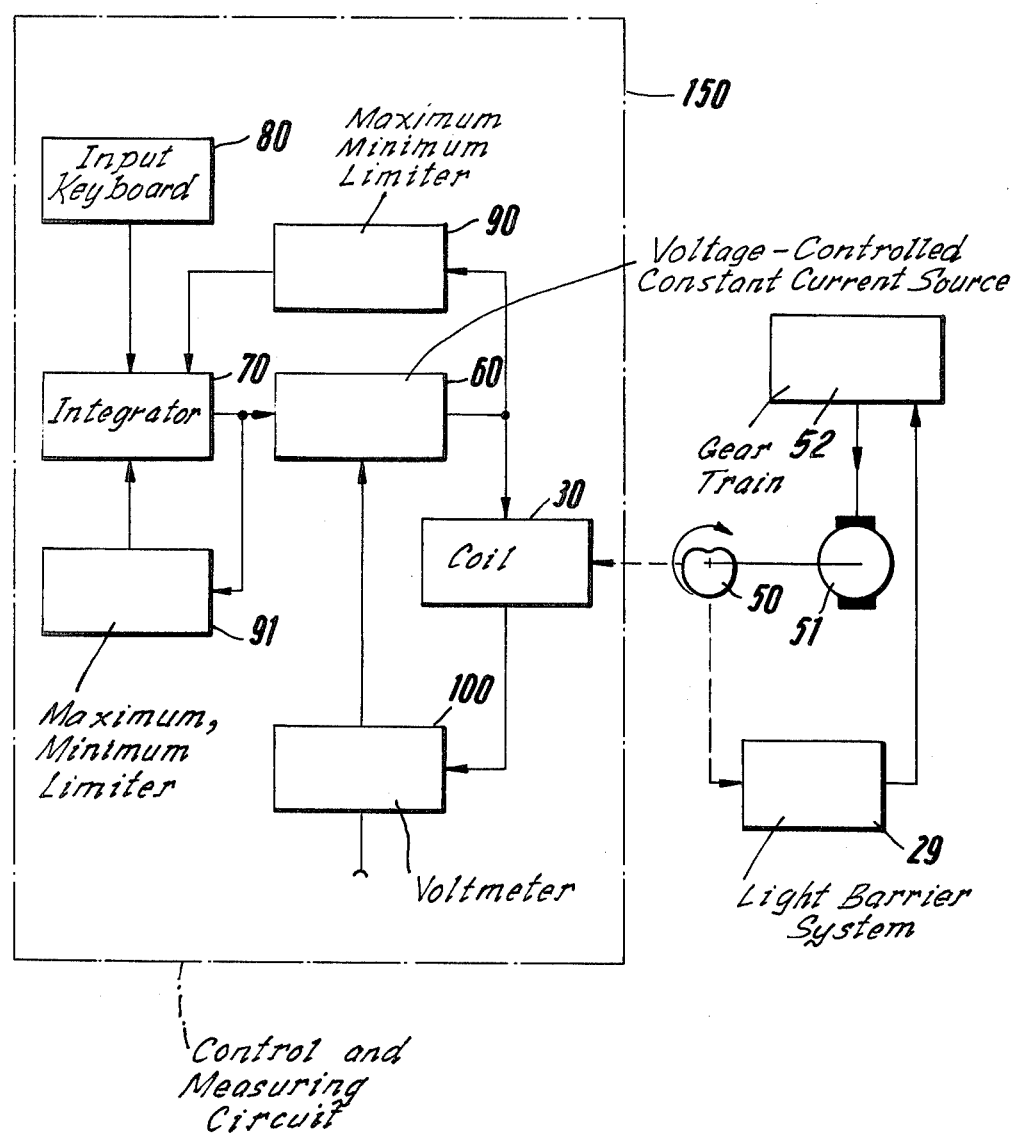
FIG. 3 is a block diagram of the electronics for control of the apparatus and for its measuring function.

FIG. 3 shows the electronics in the form of a block diagram; they consist of the control and measuring circuits 150 which are connected with the coil 30 through the gold strips 26. A voltage-controlled constant current source 60 is provided to energize coil 30. Constancy of current is necessary, because an externally superimposed movement of the system would make it behave as a generator and current and indication would be falsified. The control circuitry of the constant current source 60 prevents additionally introduced current transients. Also, good stability is attained; for instance, a change in resistance of coil 30 on account of temperature influences is irrelevant because only the voltage changes and not the effective current.

An integrator 70 with good storage capability controls the constant current source 60. The output voltage of the integrator grows with the duration of input current flow; it diminishes when the current is reversed. The setting is effected by the input keyboard 80. A key is provided for a rapid charge of the storage so far that a small negative current flows through the coil 30. This causes a force which separates the probe 25 from the body area under examination.

The integrator 70 is further affected by the maximum and minimum limiters 90, 91 which act as limit switches. They prevent further operation by the integrator 70 in case of the measuring range being exceeded.

A voltmeter serves as indicator 100. For this a digital voltmeter with data display can be used; it measures the voltage accross coil 30 which corresponds to the force. It is thus possible to represent any desired unit of force.

The motor control with its keyboard controls by means of motor 51 and gear train 52 the heart-shaped cam plate 50 which serves as detent; this cam plate 50 may also be shaped differently. In its initial position it offers its greatest radial depth to a slide 28 which is secured to the free end of the lower lever arm 20b. The coil current as set generates the force which at first is directed against the cam plate 50 whereat the probe 25 is in a retracted position. Operating a key of keyboard 80 activates the motor 51 and turns the cam plate 50 by means of the gear train 52. Slide 28 which is disposed in the operational range of the cam plate 50 rides on the outer edge of the cam plate and this profile controls the forward movement of probe 25. If the probe 25 meets an obstruction, in particular the body area under examination, the probe transfers the force to it. The cam plate 50 continues to turn until its widest part masks both sensors of the light barrier system 29 (FIG. 1). At this stage the lever 20 has its greatest freedom of movement. Upon release of the key, the cam plate 50 automatically reverses its rotation and lifts the probe 25 off the body area previously touched.

FIG. 4 represents in isometric view the initial position of the apparatus in use, particularly showing the free space, a, between probe 25 and the measuring spot.

FIG. 5 illustrates in isometric view the placement of the probe on the measuring spot.

Figure 6:
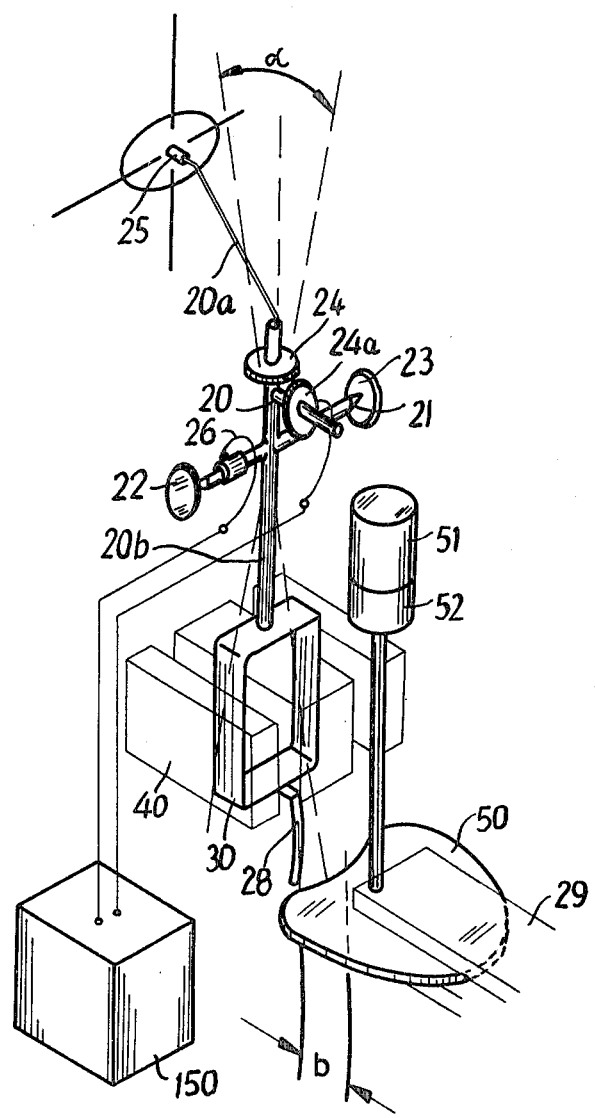

FIG. 6 shows in isometric representation the position during measurement and, in particular, the range of possible positions of the lever 20 and the free space, b, between the slide 28 and the cam plate 50.

What is claimed is:

1. An apparatus for the generation and measurement of defined forces independent of position or travel of transmitting members for medical examination appliances, said apparatus comprising:
   (a) in a housing, a two-armed lever pivotably mounted about a horizontal axis for movement in a vertical plane, the center of gravity of said lever coinciding with the pivot axis of said lever, a contact probe for engaging a body area under examination secured to the free end of the upper arm of said lever;
   (b) force producing means including a permanent magnet system and a rectangular coil disposed at the free end of a lower lever arm of said lever with said rectangular coil being affixed to said lower lever arm, said rectangular coil when moving said lever adapted to move, with at least one side portion, through a homogeneous magnetic field generated by said permanent magnet system, narrow strips of gold with a negligibly small resisting torque connecting said rectangular coil with electronic control and measuring circuitry;

(c) electronic control and measuring circuitry for energizing said coil including a voltage-controlled constant current source connected to a control integrator, an input keyboard for setting the output voltage of said electronic circuitry, maximum and minimum limiters in the form of limit switches operatively coupled to said integrator, and electromagnetic indicating means;

(d) the extent of movement of said lever about its pivot axis in the homogeneous field of said permanent magnet system adapted to being restricted;

(e) the movement of said lever being mechanically controlled by a heart-shaped cam plate serving as detent being driven by a motor and connected with a control for said motor to effect controlled movements of said contact probe;

(f) said heart-shaped cam plate being connected to said motor through an interposed gear train;

(g) within the operational range of said cam plate, a slide being secured to the free end of said lower arm of said lever and a light barrier system being disposed for movement control of said lever.

2. An apparatus as defined in claim 1 wherein said light barrier system is disposed about the profiled edge of said cam plate opposite of said slide.

3. An apparatus as defined in claim 1 wherein said upper arm of the lever is made longer than said lower arm.

* * * * *